US011992680B2

(12) United States Patent
Sumino (10) Patent No.: US 11,992,680 B2
(45) Date of Patent: May 28, 2024

(54) ELECTRICAL TREATMENT DEVICE AND TREATMENT SYSTEM

(71) Applicant: Omron Healthcare Co., Ltd., Kyoto (JP)

(72) Inventor: Teppei Sumino, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 158 days.

(21) Appl. No.: 17/100,450

(22) Filed: Nov. 20, 2020

(65) Prior Publication Data

US 2021/0069508 A1 Mar. 11, 2021

Related U.S. Application Data

(63) Continuation of application No. PCT/JP2019/014510, filed on Apr. 1, 2019.

(30) Foreign Application Priority Data

May 24, 2018 (JP) ................................. 2018-099771

(51) Int. Cl.
*A61N 1/36* (2006.01)
*A61N 1/04* (2006.01)

(52) U.S. Cl.
CPC ....... *A61N 1/36034* (2017.08); *A61N 1/0452* (2013.01); *A61N 1/0456* (2013.01); *A61N 1/0476* (2013.01); *A61N 1/36021* (2013.01)

(58) Field of Classification Search
CPC .............. A61N 1/36034; A61N 1/0452; A61N 1/0476; A61N 1/36021
See application file for complete search history.

(56) References Cited

U.S. PATENT DOCUMENTS 5,048,523 A 9/1991 Yamasawa et al.
5,702,428 A 12/1997 Tippey et al.
(Continued)

FOREIGN PATENT DOCUMENTS

DE 690 24 084 T2 8/1996
DE 693 24 680 T2 12/1999
(Continued)

OTHER PUBLICATIONS

English translation of JP 2016-073372 published on May 12, 2016 (Year: 2016).*
(Continued)

*Primary Examiner* — Allen Porter
*Assistant Examiner* — Adreanne A. Arnold
(74) *Attorney, Agent, or Firm* — Birch, Stewart, Kolasch & Birch, LLP (57) ABSTRACT

An electrical treatment device (200) includes a plurality of electrodes that come into contact with a site of a body of a user; an operation unit (302) that receives an operation for adjusting an electrical stimulation intensity provided to the site; and a treatment execution unit (304) that applies a pulse voltage corresponding to the electrical stimulation intensity to the plurality of electrodes and performs treatment of the site by changing a frequency of the pulse voltage within a predetermined frequency range continuously or in a step-like manner. When the operation unit (302) receives the operation, the treatment execution unit (304) changes the pulse voltage to correspond to the electrical stimulation intensity based on the operation, changes the frequency of the pulse voltage to a predetermined frequency, and changes the frequency of the pulse voltage from the predetermined frequency continuously or in a step-like manner.

15 Claims, 6 Drawing Sheets

(56) References Cited

U.S. PATENT DOCUMENTS

| | | | |
|---|---|---|---|
| 2004/0230253 A1 | 11/2004 | Sakagami et al. | |
| 2009/0069864 A1 | 3/2009 | Sakagami et al. | |
| 2020/0254253 A1* | 8/2020 | Samejima | ............ A61N 1/0452 |

FOREIGN PATENT DOCUMENTS

| | | |
|---|---|---|
| DE | 11 2018 004 703 T5 | 6/2020 |
| JP | 2000-14803 A | 1/2000 |
| JP | 2000-288099 A | 10/2000 |
| JP | 2004-337298 A | 12/2004 |
| JP | 2005-252449 A | 9/2005 |
| JP | 2011-15723 A | 1/2011 |
| JP | 2016-73372 A | 5/2016 |

OTHER PUBLICATIONS

German Office Action for corresponding German Application No. 112019001852.3, dated Aug. 17, 2023, with English translation.

* cited by examiner

| TIME (sec) | FREQUENCY (Hz) |
|---|---|
| 0 | 1 |
| 2 | 2 |
| 6 | 10 |
| 8 | 30 |
| 9 | 50 |
| 10 | 100 |
| 11 | 200 |
| 12 | 250 |

ELECTRICAL TREATMENT DEVICE AND TREATMENT SYSTEM

TECHNICAL FIELD

This application is the U.S. national stage application filed pursuant to 35 U.S.C. 365(c) and 120 as a continuation of International Patent Application No. PCT/JP2019/014510, filed Apr. 1, 2019, which application claims priority from Japanese Patent Application No. JP2018/09771, filed May 24, 2018, which applications are incorporated herein by reference in their entireties.

The present disclosure relates to an electrical treatment device and a treatment system.

BACKGROUND ART

There have been known electrical treatment devices configured to relieve stiffness and pain. Such electrical treatment devices provide stimulation by outputting an electrical signal to muscles via an electrode, the electrode being in contact with an affected portion.

For example, JP 2011-15723 A (Patent Document 1) describes an electronic treatment device that relieves stiffness and pain by stimulating muscles and nerves via a current flowing through the body. The electronic treatment device outputs, from an element, via a pulse signal with a repetition frequency that repeatedly varies continuously or in a step-like manner, between a first frequency and a second frequency lower than the first frequency, a modulated wave with a modulated carrier wave of a third frequency higher than the first frequency.

CITATION LIST

Patent Literature

SUMMARY OF INVENTION

Technical Problem

The electronic treatment device according to Patent Document 1 performs stimulation by varying frequencies of a stimulation signal. In this manner, with the electrical stimulation varying in frequency within a predetermined frequency range, the user feels a varying degree of electrical stimulation. Patent Document 1 describes that a power level setting by a HI switch and a LOW switch can be received at any time during the operation of the electronic treatment device.

Thus, it is believed that in the case in which a HI switch operation is received to increase the power level during operation of the electronic treatment device, the power level is increased while changing the frequency of the stimulation signal. In this case, when the operation to increase the power level is not performed at the timing at which the frequency changes in the direction of an increase in the electrical stimulation, the user may receive an unintended electrical stimulation (for example, an overly strong stimulation or the like). This may cause the user to feel uncomfortable.

An object of an aspect of the present disclosure is to provide, with an electrical treatment device with varying frequencies of pulse voltage, an electrical treatment device and a treatment system capable of providing treatment aligned with user intentions when an operation to change the strength of an electrical stimulation is performed.

Solution to Problem

An example of the present disclosure is an electrical treatment device that includes: a plurality of electrodes that come into contact with a site of a body of a user; an operation unit that receives an operation for adjusting an electrical stimulation intensity provided to the site; and a treatment execution unit that applies a pulse voltage corresponding to the electrical stimulation intensity to the plurality of electrodes and performs treatment of the site by changing a frequency of the pulse voltage within a predetermined frequency range continuously or in a step-like manner. When the operation unit receives the operation, the treatment execution unit changes the pulse voltage to correspond to the electrical stimulation intensity based on the operation and changes the frequency of the pulse voltage to a predetermined frequency and changes the changed frequency of the pulse voltage from the predetermined frequency continuously or in a step-like manner.

According to the configuration described above, treatment aligned with user intentions can be provided when an operation to change the strength of an electrical stimulation is performed using an electrical treatment device with varying frequencies of pulse voltage.

In another example of the present disclosure, the predetermined frequency is a frequency other than a maximum frequency of the predetermined frequency range.

According to the configuration described above, when changing the electrical stimulation intensity, it is possible to prevent a stimulation that is too strong from being provided to the user.

In another example of the present disclosure, the predetermined frequency is a minimum frequency of the predetermined frequency range. According to the configuration described above, when changing the electrical stimulation intensity, it is possible to prevent a strong stimulation from being provided to the user.

In an example of the present disclosure, the predetermined frequency is a frequency at a predetermined time prior to a time point when a frequency of a pulse voltage reaches the maximum frequency.

According to the configuration described above, when changing the electrical stimulation intensity, it is possible to reduce the time delay to reach the maximum frequency without providing too strong of a stimulation to the user.

In another example of the present disclosure, the treatment execution unit changes the frequency of the pulse voltage, in the frequency range, by sweeping the frequency in increasing direction from a minimum frequency to a maximum frequency and then by sweeping the frequency in decreasing direction from the maximum frequency to the minimum frequency.

According to this configuration, the electrical stimulation felt by the user is gradually increased, which makes it possible to further reduce the possibility of causing discomfort to the user.

In another example of the present disclosure, the electrical treatment device further includes a difference calculation unit that, when the operation is received by the operation unit, calculates a difference frequency between a frequency of a pulse voltage just before the operation is received and the predetermined frequency. The treatment execution unit, if the difference frequency is less than a threshold, changes the frequency of the pulse voltage to the predetermined frequency and changes the frequency of the pulse voltage from the predetermined frequency continuously or in a step-like manner and, if the difference frequency is equal to or greater than the threshold, changes the frequency of the pulse voltage just before by only a predetermined value to approach the predetermined frequency and changes the frequency of the pulse voltage from a frequency after change continuously or in a step-like manner.

According to the configuration described above, a sudden change in frequency can be prevented when changing the electrical stimulation intensity, and thus, it is possible to prevent discomfort to the user.

In another example of the present disclosure, the electrical treatment device is a low-frequency treatment device.

According to this configuration, the user can receive treatment in a more appropriate frequency range.

In another example of the present disclosure, a treatment system includes: an electrical treatment device including a plurality of electrodes that come into contact with a site of a body of a user; and a terminal device capable of wireless communication with the electrical treatment device. The terminal device receives operations for adjusting the electrical stimulation intensity provided to the site and transmits a signal indicating the operation to the electrical treatment device. The electrical treatment device includes a treatment execution unit that applies a pulse voltage corresponding to the electrical stimulation intensity to the plurality of electrodes and executes treatment of the site by varying the frequency of the pulse voltage within the predetermined frequency range continuously or in a step-like manner. When the operation is performed, the treatment execution unit changes the pulse voltage to correspond to the electrical stimulation intensity based on the operation, changes the frequency of the pulse voltage to a predetermined frequency, and changes the frequency of the pulse voltage from the predetermined frequency continuously or in a step-like manner.

With an electrical treatment device with varying pulse voltage frequencies, treatment aligned with user intentions can be provided when an operation to change the strength of an electrical stimulation is performed.

Advantageous Effects of Invention

According to the present disclosure, with an electrical treatment device with varying frequencies of pulse voltage, treatment aligned with user intentions can be provided when an operation to change the strength of an electrical stimulation is performed.

DESCRIPTION OF EMBODIMENTS

Embodiments of the present invention will be described below with reference to the drawings. In the following description, like components are given like numerals. Names and functions thereof are also the same. Thus, the detailed description of such components is not repeated.

Application Example

Figure 1:
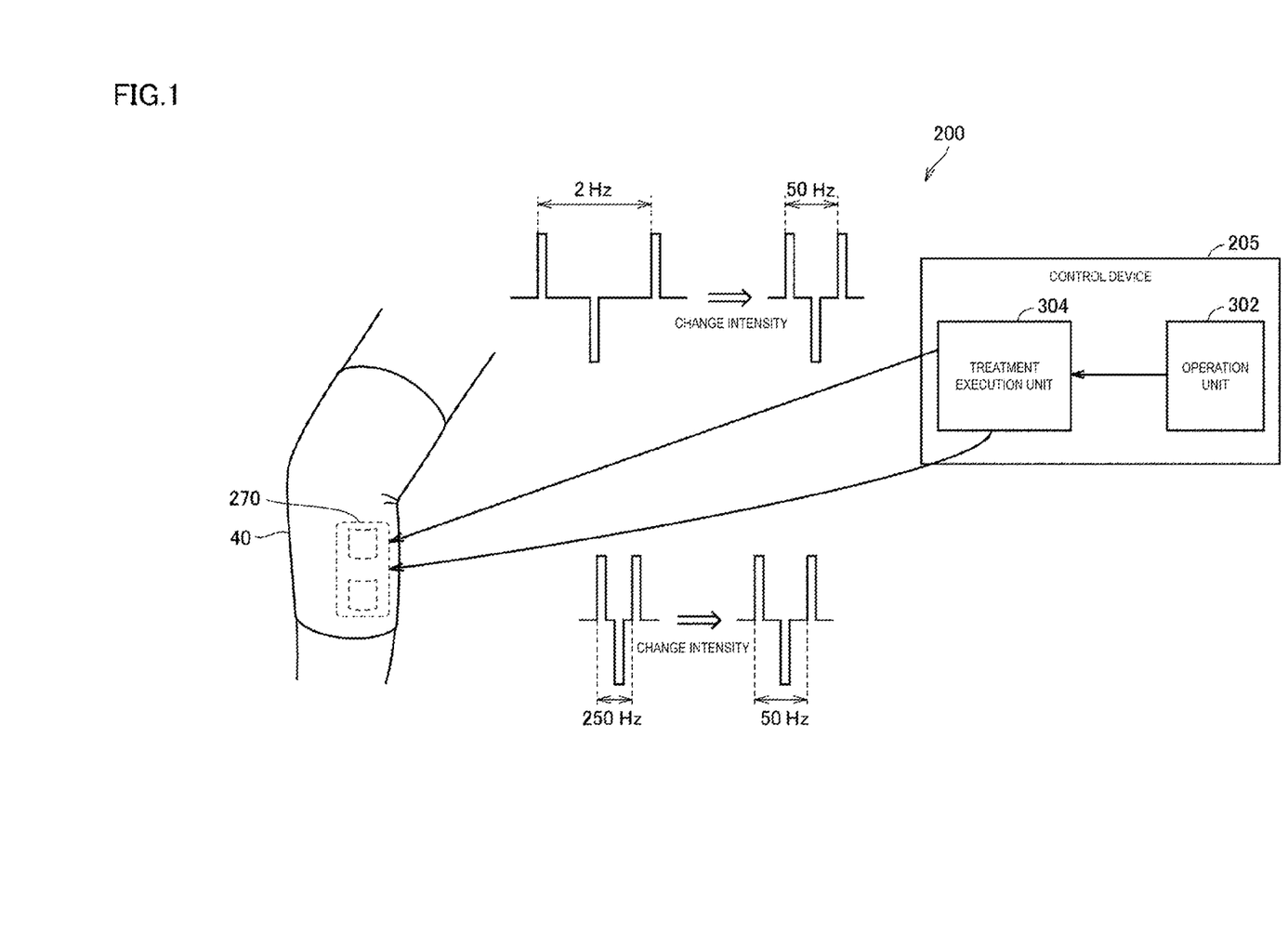
FIG. 1 is a diagram illustrating an electrical treatment device according to the present embodiment.

An application example of the present invention will be described with reference to FIG. 1. FIG. 1 is a diagram illustrating an electrical treatment device 200 according to the present embodiment.

Referring to FIG. 1, the electrical treatment device 200 includes a control device 205, i.e., a main body portion, and a pair of pads 270 that are stuck to the treatment site (for example, the knee region). The control device 205 and the pads 270 are electrically connected by a cord. A supporter 40 is a knee supporter that entirely covers the knee region of a user.

The electrical treatment device 200 is a low-frequency treatment device that performs treatment such as alleviating knee pain and easing shoulder stiffness of the user by supplying a low-frequency pulse current, for example. The frequency of the low-frequency pulse current is, for example, from 1 Hz to 1200 Hz.

The pads 270 have a sheet-like shape and are configured to attach to the user's body. The surface on one side of the pad 270 (the surface that does not come into contact with the body) is provided with a plug that corresponds to an electrode (not illustrated) formed on the surface on the other side (the surface that comes into contact with the body). The electrode is formed from a conductive gel-like material, for example.

The control device 205 includes, as main components, an operation unit 302 and a treatment execution unit 304.

The operation unit 302 receives various instructions regarding the treatment content from the user. Specifically, the operation unit 302 receives an operation for adjusting the electrical stimulation intensity from the user. The electrical stimulation intensity can be set to a plurality of levels. In this embodiment, for example, the electrical stimulation intensity can be set to 20 levels, from the minimum intensity level "1" to the maximum intensity level "20". The user can use the operation unit 302 to set the desired electrical stimulation intensity by increasing or decreasing the level of the electrical stimulation intensity.

The treatment execution unit 304 controls the pulse voltage applied to electrodes of the pair of pads 270 that come into contact with the site (for example, knee) on the user's body according to a treatment instruction from the user and performs treatment on the knee. The treatment execution unit 304 outputs a pulse voltage with a frequency that repeatedly varies within a predetermined frequency range K (for example, from 1 Hz to 250 Hz) in a step-like manner.

Figure 2:
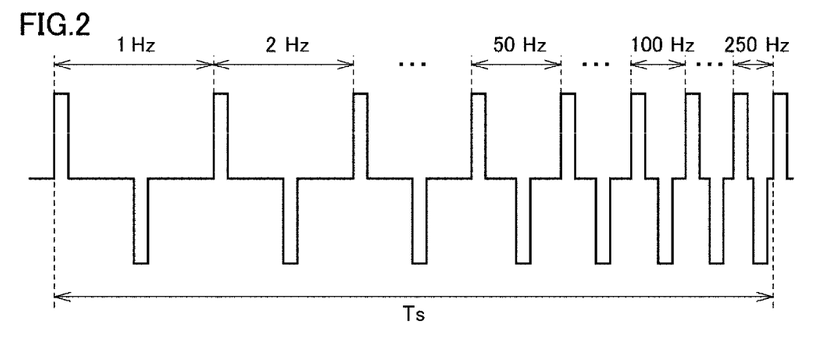
FIG. 2 is a diagram illustrating an example of a voltage waveform of a pulse voltage according to the present embodiment.

FIG. 2 is a diagram illustrating an example of a voltage waveform of a pulse voltage according to the present embodiment. Referring to FIG. 2, a voltage waveform of the pulse voltage output by the treatment execution unit 304 is a sweep waveform that increases in a step-like manner from 1 Hz to 250 Hz in a time period Ts and then decreases in a step-like manner from 250 Hz to 1 Hz in the next time period Ts. Also, in one period, positive and negative pulses are output.

For the electrical treatment device 200, the frequency range K (1 Hz to 250 Hz) is a frequency range preset for the electrical treatment device 200 and is used as the frequency range when performing treatment using a sweep waveform with a repeatedly varying frequency. The frequency of the pulse voltage (hereinafter also referred to as the "pulse frequency") changes in the time period Ts, for example, as illustrated in FIG. 3.

Figure 3:
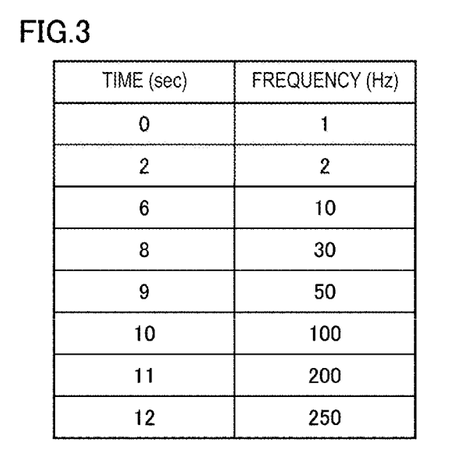
FIG. 3 is a diagram illustrating an example of the change over time of a frequency of a pulse voltage according to the present embodiment.

FIG. 3 is a diagram illustrating an example of the change over time of a frequency of a pulse voltage according to the present embodiment. Here, the time period Ts is 12 seconds. Referring to FIG. 3, for the period of time from the start time point (i.e., 0 seconds) to less than 2 seconds, for the period of time from 2 seconds to less than 6 seconds, and for the period of time from 6 seconds to less than 8 seconds, the pulse frequency is 1 Hz, 2 Hz, and 10 Hz, respectively. Following from this, every 1 second, the pulse frequency varies stepwise to 30 Hz, 50 Hz, 100 Hz, 200 Hz, and 250 Hz. However, the pulse frequency may be configured to vary continuously. For example, the pulse frequency may vary linearly or may vary in a curvilinear manner.

Going back to FIG. 1, the treatment execution unit 304 applies, to the pair of pads 270, a pulse voltage that corresponds to the electrical stimulation intensity based on an adjustment operation of the electrical stimulation intensity received by the operation unit 302 (hereinafter, also simply referred to as an "adjustment operation"). For example, the treatment execution unit 304 discretely increases or decreases the amplitude value of the pulse voltage every time the electrical stimulation intensity increases or decreases by one level.

Also, in the case in which the operation unit 302 receives the adjustment operation, the treatment execution unit 304 changes the pulse frequency to a predetermined frequency Fs (for example, 50 Hz) and changes the pulse frequency continuously or in a step-like manner from the predetermined frequency Fs.

As an example, the pulse frequency just before the adjustment operation is performed is 2 Hz. In this case, when the adjustment operation is performed, the treatment execution unit 304 changes the pulse frequency from 2 Hz to 50 Hz and changes from the changed 50 Hz in a step-like manner. Typically, the treatment execution unit 304 increases the pulse frequency from 50 Hz in a step-like manner. As another example, the pulse frequency just before the adjustment operation is performed is 250 Hz. In this case, when the adjustment operation is performed, the treatment execution unit 304 changes the pulse frequency from 250 Hz to 50 Hz and increases from the changed 50 Hz in a step-like manner.

The control described above can prevent the user from being provided with an unintentional strong stimulation when the user performs an operation that adjusts the electrical stimulation intensity, even in the case in which the pulse frequency varies repeatedly.

For example, a flow is envisioned in which the pads 270 are attached to the knee while the user is sitting, the electrical stimulation intensity is increased, and the user stands up and walks. Typically, the greater the amplitude value of the pulse voltage, the greater the pulse width of the pulse voltage, and the higher the pulse frequency, the more likely the user is to feel a strong electrical stimulation.

As in the related art, in the case in which the pulse frequency varies repeatedly regardless of an adjustment operation of the electrical stimulation intensity, because the pulse frequency remains in a low frequency region (for example, from 1 Hz to 10 Hz) when the user is sitting (in other words, because it is relatively harder to feel the electrical stimulation), the user increases the electrical stimulation intensity to a desired electrical stimulation. In addition, because the pulse frequency remains in a high frequency region (for example, from 200 Hz to 250 Hz) when the user starts walking (in other words, because a strong electric stimulation is easy to feel), the electrical stimulation intensity set earlier may be too strong and cause the user to feel discomfort or be surprised.

On the other hand, with the electrical treatment device 200 according to the present embodiment, each time the adjustment operation of the electrical stimulation intensity is performed, the pulse frequency is changed to the predetermined frequency Fs and increases from the predetermined frequency Fs in a step-like manner. In this way, by the pulse frequency being changed to a moderate frequency when the electrical stimulation intensity is changed, the user increasing the electrical stimulation intensity too high can be prevented. In addition, even in the case in which an operation of increasing the electrical stimulation intensity is performed just before the pulse frequency transitions to the high frequency region, it is also possible to prevent the user from being provided with an unintentional strong electrical stimulation. In this way, the electrical treatment device 200 can perform treatment aligned with the intentions of the user.

Configuration Example

First Embodiment

Appearance

Figure 4:
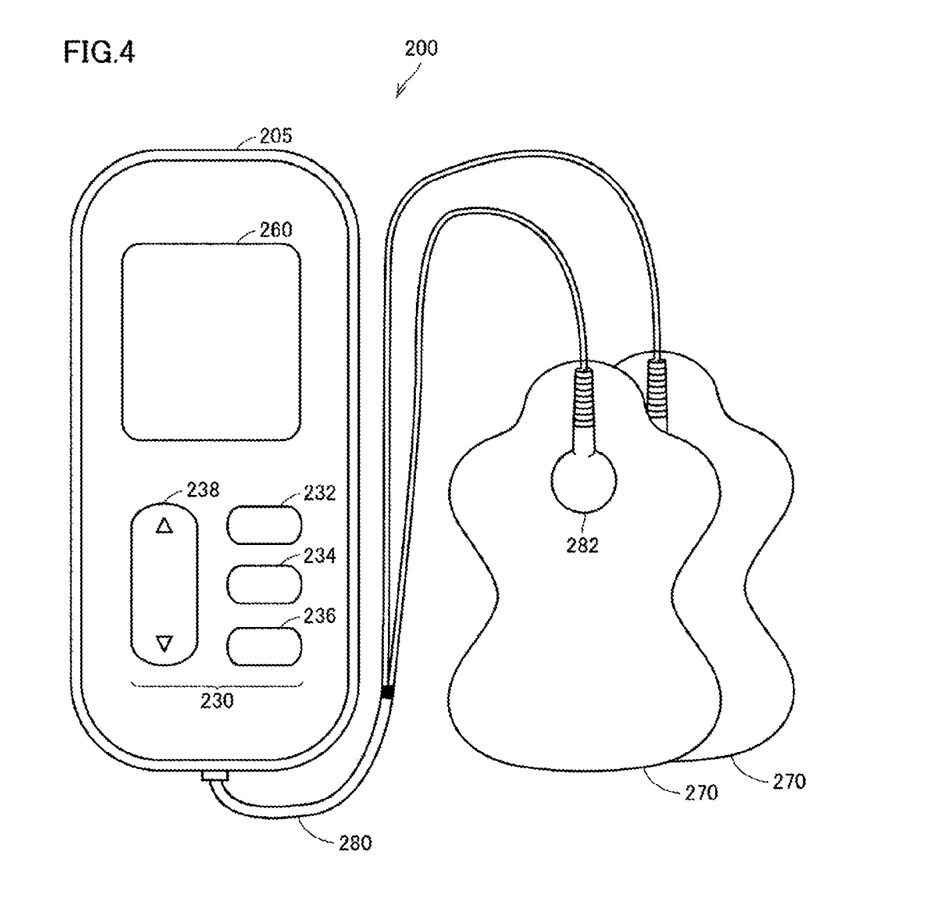
FIG. 4 is a diagram illustrating an example of the appearance of the electrical treatment device according to the first embodiment.

FIG. 4 is a diagram illustrating an example of the appearance of the electrical treatment device 200 according to the first embodiment. Referring to FIG. 4, the electrical treatment device 200 includes the control device 205, the pair of pads 270, and a cord 280 for electrically connecting together the control device 205 and the pads 270.

The control device 205 and the pads 270 are connected together by connecting together a plug 282 of the cord 280 and the plug on the pad 270 and inserting the cord 280 into the jack of the control device 205. Note that when the polarity of the electrode formed on one of the pads 270 is positive, the polarity of the electrode formed on the other pad 270 is negative.

The control device 205 is provided with an operation interface 230 constituted by various buttons and a display 260. The operation interface 230 includes a power button 232 for switching the power source on and off, a mode selection button 234 for selecting a treatment mode, a treatment start button 236, and an adjustment button 238 for adjusting the electrical stimulation intensity. Note that the operation interface 230 is not limited to the configuration described above and may have configuration including other buttons, dials, switches, and the like.

The electrical stimulation intensity, the remaining treatment time, the treatment mode, the mounting state of the pads 270, and the like are displayed on the display 260. Various messages are also displayed on the display 260.

Hardware Configuration

Figure 5:
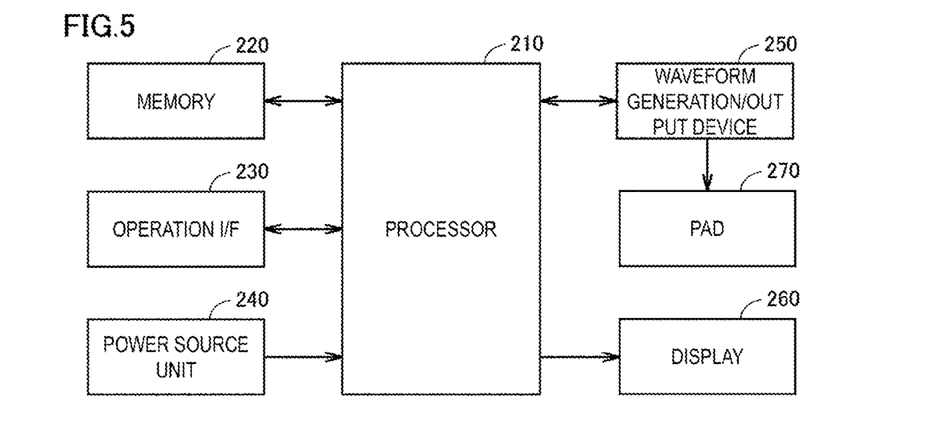
FIG. 5 is a block diagram illustrating an example of a hardware configuration of the electrical treatment device according to the first embodiment.

FIG. 5 is a block diagram illustrating an example of a hardware configuration of the electrical treatment device 200 according to the first embodiment. Referring to FIG. 5, the control device 205 of the electrical treatment device 200 includes a processor 210, a memory 220, the operation interface 230, a power source unit 240, a waveform generation/output device 250, and the display 260. The control device 205 is connected to the pair of pads 270.

The processor 210 typically may be an arithmetic processing unit such as a central processing unit (CPU) or a multi processing unit (MPU). The processor 210 functions as a control unit that controls the operation of components of the electrical treatment device 200 by reading out and executing a program stored in the memory 220. By executing the program, the processor 210 realizes each of processing (steps) of the electrical treatment device 200 described later.

The memory 220 is realized by random access memory (RAM), read-only memory (ROM), flash memory, and the like. The memory 220 stores programs executed by the processor 210, data used by the processor 210, and the like.

The operation interface 230 receives an operation input to the electrical treatment device 200 and includes various buttons such as those described above. When the user operates various buttons, a signal corresponding to the operation is input to the processor 210.

The power source unit 240 supplies power to the constituent elements of the electrical treatment device 200. As the power source, an alkaline battery or a rechargeable battery, such as a lithium ion battery or nickel hydrogen battery may be used, for example. The power source stabilizes a battery voltage and generates a drive voltage that is supplied to the components.

The waveform generation/output device 250 outputs a current (also referred to below as a "treatment current") to a treatment site on the user's body through the pads 270. The waveform generation/output device 250 includes a booster circuit, a voltage adjustment circuit, an output circuit, a current detection circuit, and the like.

The booster circuit boosts the power supply voltage to a predetermined voltage. The voltage adjustment circuit adjusts the voltage boosted by the booster circuit to a voltage corresponding to the electrical stimulation intensity set by the user. Specifically, the electrical stimulation intensity of the electrical treatment device 200 can be adjusted to a predetermined number of levels (for example, 20 levels) by the adjustment button 238. For example, after selecting the power button 232 and turning the power of the electrical treatment device 200 on, the electrical stimulation intensity is set to a level "1" when the adjustment button 238 is pressed once.

Typically, the processor 210 executes control to raise the level of the electrical stimulation intensity by one in response to an operation (increase operation) of one push of the increase button of the adjustment button 238 and control to lower the level of the electrical stimulation intensity by one in response to an operation (decrease operation) of one push of the decrease button of the adjustment button 238.

The processor 210 receives a setting input of the electrical stimulation intensity via the adjustment button 238 and instructs the waveform generation/output device 250 (voltage adjustment circuit) to adjust to a voltage corresponding to the received electrical stimulation intensity.

The output circuit generates a treatment waveform (pulse waveform) corresponding to the treatment mode on the basis of the voltage adjusted by the voltage adjustment circuit and outputs the treatment waveform to (the electrodes of) the pads 270 via the cord 280. Specifically, when the user performs an operation, such as switching the treatment mode or changing the electrical stimulation intensity, via the operation interface 230, a control signal corresponding to the operation content is input to the output circuit from the processor 210. The output circuit outputs a treatment waveform according to the control signal.

In this example, the electrical treatment device 200 is provided with a plurality of treatment modes in advance. The treatment modes include, for example, "massage", "tap", and "press".

The output circuit can generate an electrical stimulation corresponding to various modes including "massage", "tap", and "press" by varying the waveform of the pulses (including pulse width, pulse interval, frequency, and output polarity). Also, in the present embodiment, by changing the amplitude of the pulse voltage, the output circuit adjusts the electrical stimulation intensity. For example, the output circuit increases the electrical stimulation intensity by increasing the amplitude value and reduces the electrical stimulation intensity by reducing the amplitude value. Note that the output circuit may have a configuration in which the electrical stimulation intensity is adjusted by changing the pulse width. For example, the output circuit increases the electrical stimulation intensity by increasing the pulse width and reduces the electrical stimulation intensity by reducing the pulse width. Specifically, a known voltage waveform can be used as the pulse voltage waveform.

The current detection circuit detects a value for the current flowing between the pair of pads 270 and inputs a signal indicating the detected value to the processor 210. The processor 210 can detect whether the pads 270 are attached to the user or whether the pads 270 are not attached to the user, using the current value input from the current detection circuit. For example, when the current value is a predetermined value or greater, the processor 210 determines that a plurality of the electrodes are in contact (in other words, the pair of pads 270 are attached to the user). When the current value is less than a predetermined value, the processor 210 determines that at least one of the plurality of electrodes is not in contact (at least one of the pair of pads 270 is not attached to the user).

The display 260 is constituted of, for example, a liquid crystal display (LCD) and displays various information in accordance with an instruction from the processor 210.

Functional Configuration

Figure 6:
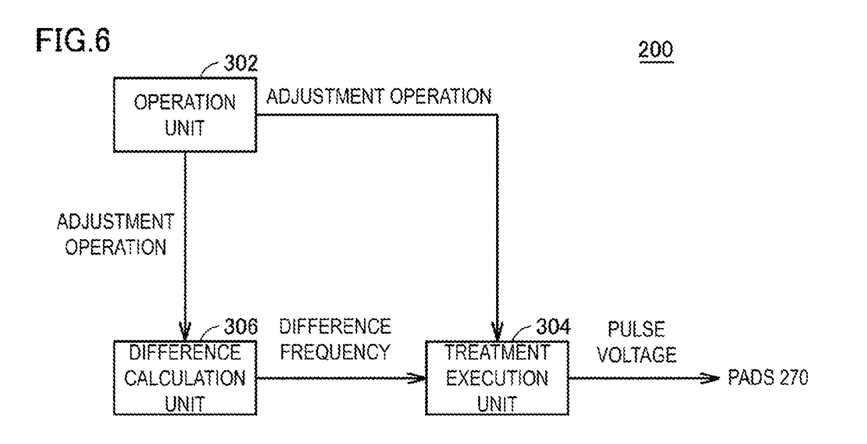
FIG. 6 is a block diagram illustrating an example of the functional configuration of the electrical treatment device according to the first embodiment.

FIG. 6 is a block diagram illustrating an example of the functional configuration of the electrical treatment device 200 according to the first embodiment. Referring to FIG. 6, the electrical treatment device 200 includes the operation unit 302, the treatment execution unit 304, and a difference calculation unit 306.

The operation unit 302 receives an operation for adjusting the electrical stimulation intensity provided to a site via the plurality of electrodes (that is, the pair of pads 270) that are brought into contact with the site of the user's body. Typically, the operation unit 302 is realized by the processor 210 and the operation interface 230.

The treatment execution unit 304 applies a pulse voltage corresponding to the electrical stimulation intensity to the plurality of electrodes and executes treatment of the site on the body by varying the pulse frequency within the frequency range K continuously or in a step-like manner. Typically, the treatment execution unit 304 varies the pulse frequency, in the frequency range K, by sweeping the frequency in an increasing direction from the minimum frequency to the maximum frequency and then by sweeping the frequency in a decreasing direction from the maximum frequency to the minimum frequency.

In certain aspects, in response of an adjustment operation of the electrical stimulation intensity, the treatment execution unit 304 changes the pulse voltage to correspond to the electrical stimulation intensity on the basis of the adjustment operation, changes the pulse frequency to the predetermined frequency Fs, and changes the pulse frequency from the predetermined frequency Fs continuously or in a step-like manner. More specifically, the treatment execution unit 304 increases the pulse frequency continuously or in a step-like manner from the predetermined frequency Fs.

The predetermined frequency Fs is a frequency other than the maximum frequency in the frequency range K (for example, 250 Hz). An example of the predetermined frequency Fs is the minimum frequency in the frequency range K (for example, 1 Hz). In this way, the pulse frequency is always be the minimum value when the electrical stimulation intensity is changed, and thus it is possible to prevent a strong stimulation from being provided to the user.

Another example of the predetermined frequency Fs is a frequency (for example, 50 Hz) at a predetermined time (for example, 3 seconds) prior to a time point when the pulse frequency reaches the maximum frequency (for example, 250 Hz). In this way, by changing the pulse frequency to a moderate frequency when changing the electrical stimulation intensity, it is possible to reduce the time delay to reach the maximum frequency without providing too strong of a stimulation to the user.

In another aspect, the treatment execution unit 304 may change the pulse frequency in accordance with a difference between the pulse frequency just prior to receiving an adjustment operation of the electrical stimulation intensity and the predetermined frequency.

Specifically, in response to an adjustment operation of the electrical stimulation intensity, the difference calculation unit 306 calculates a difference frequency between the pulse frequency just before the adjustment operation and the predetermined frequency Fs. The difference calculation unit 306 outputs the calculated difference frequency to the treatment execution unit 304. Note that the difference frequency is an absolute value.

In the case in which the difference frequency is less than a threshold Th, the treatment execution unit 304 changes the pulse frequency to the predetermined frequency Fs and changes the pulse frequency continuously or in a step-like manner from the predetermined frequency Fs. In this example, the predetermined frequency Fs is 50 Hz and the threshold Th is 30 Hz. In the case in which the pulse frequency just before is 30 Hz and the difference frequency is 20 Hz (<the threshold Th), the pulse frequency is changed to the predetermined frequency Fs. In addition, in the case in which the pulse frequency just before is 70 Hz and the difference frequency is 20 Hz (<the threshold Th), the pulse frequency is changed to the predetermined frequency Fs.

On the other hand, in the case in which the difference frequency is equal to or greater than the threshold Th, the treatment execution unit 304 changes the pulse frequency just before by only a predetermined value to approach the predetermined frequency Fs and changes the frequency of the pulse voltage from the changed frequency continuously or in a step-like manner.

In this example, as in the example described above, the predetermined frequency Fs is 50 Hz and the threshold Th is 30 Hz. At this time, in the case in which the pulse frequency just before is 10 Hz and the difference frequency is 40 Hz (>the threshold Th), the pulse frequency is changed by only a predetermined value in a direction approaching the predetermined frequency Fs. Typically, the predetermined value is the same as the threshold Th. In this case, the pulse frequency after change is 40 Hz. Also, in the case in which the pulse frequency just before is 100 Hz and the difference frequency is 50 Hz (>the threshold Th), the pulse frequency is changed by only 30 Hz in a direction approaching the predetermined frequency Fs, and the pulse frequency after change is 70 Hz. Note that the predetermined value is only required to be equal to or less than the threshold Th.

Processing Procedure

Figure 7:
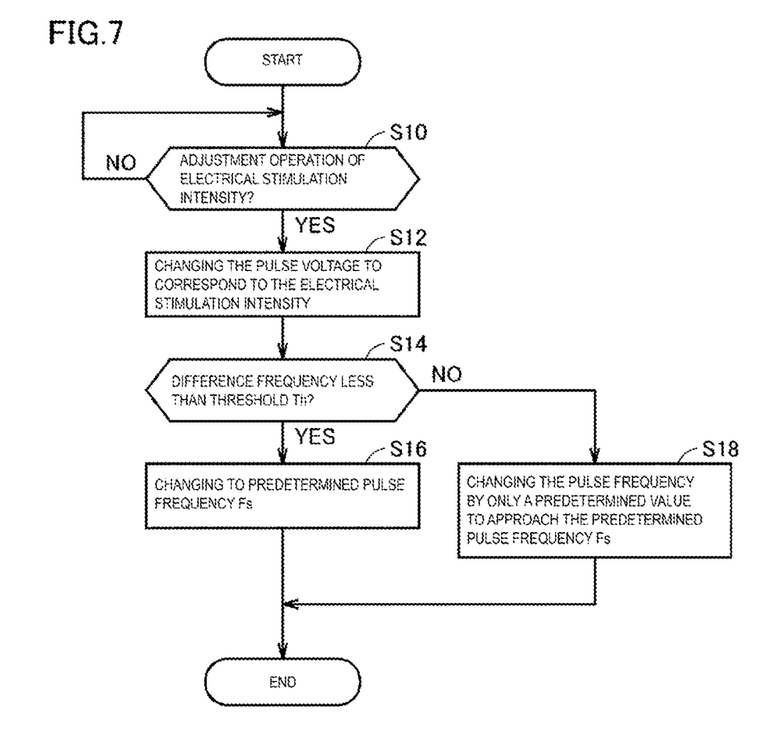
FIG. 7 is a flowchart illustrating an example of a processing procedure of the electrical treatment device according to the first embodiment.

FIG. 7 is a flowchart illustrating an example of a processing procedure of the electrical treatment device 200 according to the first embodiment. Each step in FIG. 7 is mainly performed by the processor 210 of the electrical treatment device 200.

Referring to FIG. 7, the electrical treatment device 200 determines whether or not an adjustment operation of the electrical stimulation intensity has been received through the operation interface 230 (step S10). If the adjustment operation has not been received (NO in step S10), then the electrical treatment device 200 repeats the process of step S10. If an adjustment operation has been received (YES in step S10), the electrical treatment device 200 changes the pulse voltage to correspond to the electrical stimulation intensity based on the adjustment operation (step S12). Typically, the electrical treatment device 200 changes the amplitude value of the pulse voltage to correspond to the electrical stimulation intensity.

The electrical treatment device 200 determines whether or not the difference frequency between the pulse frequency just before the adjustment operation and the predetermined frequency Fs is less than the threshold Th (step S14). If the difference frequency is less than the threshold Th (YES in step S14), the electrical treatment device 200 changes the pulse frequency to the predetermined frequency Fs (step S16). In this case, the electrical treatment device 200 changes the pulse frequency continuously or in a step-like manner from the predetermined frequency Fs.

If the difference frequency is equal to or greater than the threshold Th (NO in step S14), the electrical treatment device 200 changes the pulse frequency by only a predetermined value to approach the predetermined frequency Fs (step S18). In this case, the electrical treatment device 200 changes the pulse frequency continuously or in a step-like manner from the changed frequency.

Second Embodiment

System Configuration

The first embodiment described above has a configuration in which the user is performed treatment with a single electrical treatment device. A second embodiment having a configuration in which a terminal device and an electrical treatment device are wirelessly connected and the electrical treatment device performs treatment in accordance with an instruction from the terminal apparatus will be described. Note that the terminal device mainly serves as the operation interface 230 and the display 260 of the electrical treatment device 200 according to the first embodiment.

Figure 8:
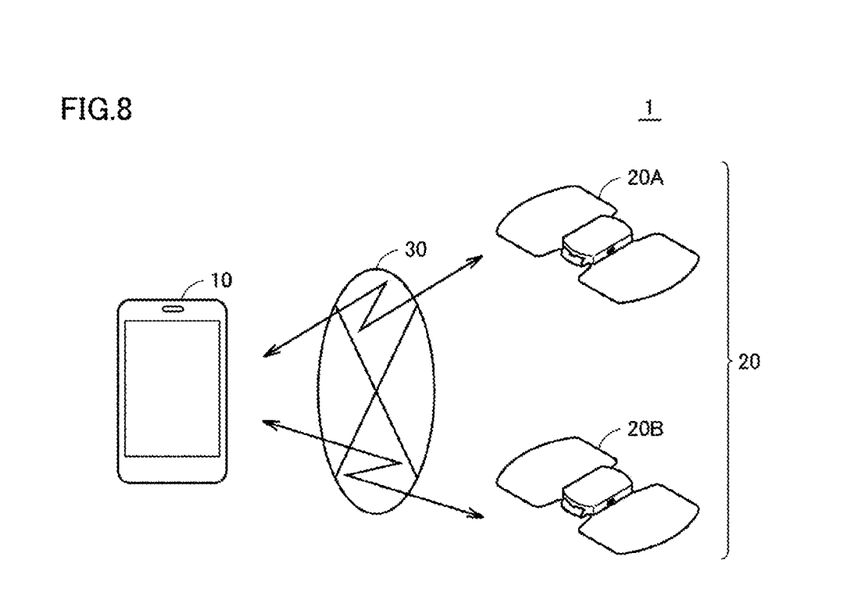
FIG. 8 is a diagram illustrating a schematic configuration of a treatment system according to a second embodiment.

FIG. 8 is a diagram illustrating a schematic configuration of a treatment system 1 according to the second embodiment. Referring to FIG. 8, the treatment system 1 includes a terminal device 10, which is a user terminal, electrical treatment devices 20A, 20B, and a network 30. Hereinafter, when describing configurations and functions shared by the electrical treatment devices 20A, 20B, the electrical treatment devices 20A, 20B are collectively referred to as an "electrical treatment device 20".

The electrical treatment device 20 is a cordless type and includes a pad, a holder, and a main body portion that are united as a single unit when used. These portions are used in combination to perform treatment. The specific configuration of the electrical treatment device 20 will be described later.

The terminal device 10 is, for example, a smart phone including a touch panel. In the description hereinafter, a smartphone will be used as a representative example of the "terminal device". However, the terminal device may be a different terminal device such as a folding type mobile telephone, a tablet terminal device, a personal computer (PC), and the like.

The network 30 for connecting the terminal device 10 and the electrical treatment device 20 employs a short-range wireless communication system, typically Bluetooth (trade name) low energy (BLE). As such, the terminal device 10 and the electrical treatment device 20 are BLE devices having a function of performing wireless communication using BLE. However, the network 30 is not limited thereto, and a different wireless communication system, such as Bluetooth (trade name) or a wireless local area network (LAN), may be employed.

In the treatment system 1 according to the second embodiment, the terminal device 10 gives instructions to the electrical treatment devices 20A and 20B connected in pairing by using an application installed on the terminal device 10. The terminal device 10 displays various kinds of information on a display 158 of the terminal device 10 and notifies the user of necessary information. For example, the terminal device 10 may display information received from the electrical treatment device 20 on the display 158.

Configuration of Electrical Treatment Device 20

Figure 9:
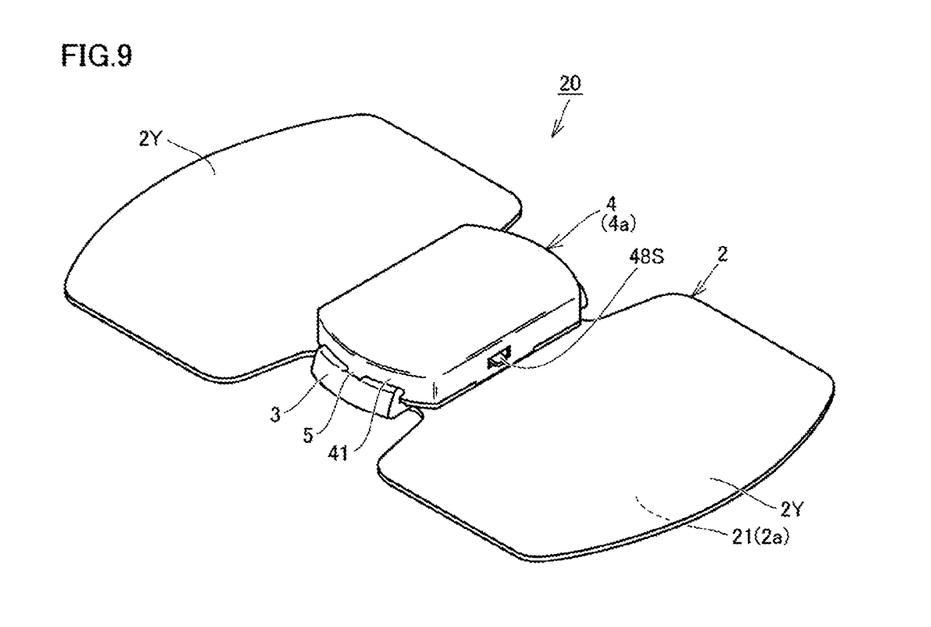
FIG. 9 is a perspective view illustrating an example of the configuration of an electrical treatment device according to the second embodiment.
Figure 10:
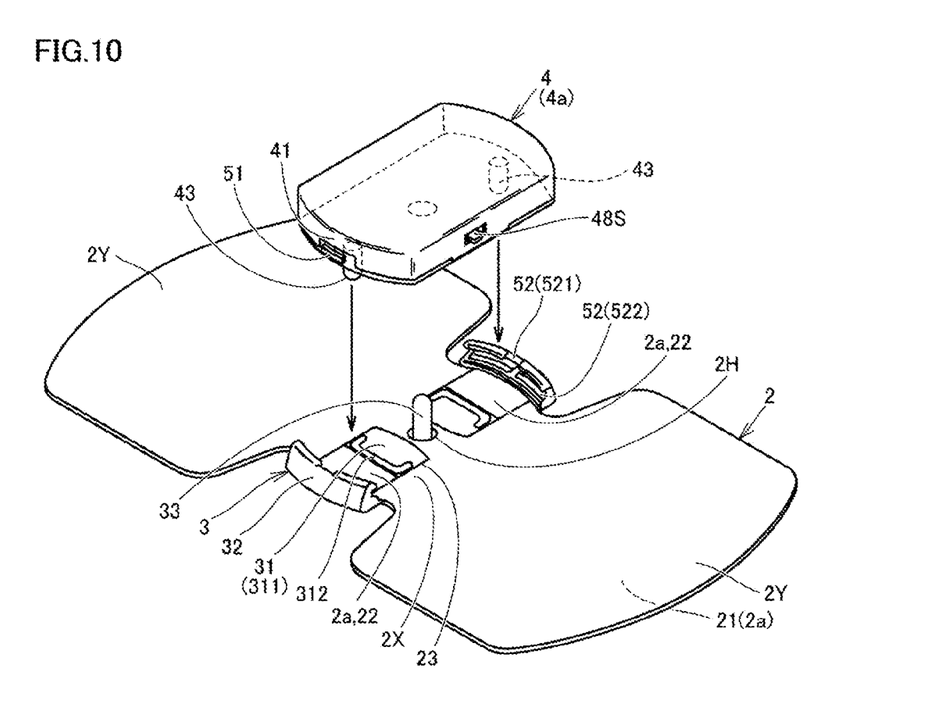
FIG. 10 is a perspective view illustrating a main body portion 4, a holder 3, and a pad 2 of the electrical treatment device according to the second embodiment, in a state where the main body portion 4 is separated from the holder 3 and the pad 2.

FIG. 9 is a perspective view illustrating an example of the configuration of the electrical treatment device 20 according to the second embodiment. FIG. 10 is a perspective view illustrating a main body portion 4, a holder 3, and a pad 2 of the electrical treatment device 20 according to the second embodiment, in a state where the main body portion 4 is separated from the holder 3 and the pad 2.

Referring to FIGS. 9 and 10, the electrical treatment device 20 is a so-called cordless type low-frequency treatment device and includes the pad 2, the holder 3, and the main body portion 4.

The pad 2 has a sheet-like shape and is configured to attach to the user's body. A conductive layer 2a is provided on a surface of a body-side portion 21 (lower surface), of the outer surfaces of the pad 2, that faces the body. The pad 2 is stuck to the user's skin by using a conductive gel or the like, and a low-frequency pulse current is supplied to the user through the conductive layer 2a.

Referring to FIG. 10, the pad 2 includes an attachment portion 2X and a treatment portion 2Y. The attachment portion 2X is held by the holder 3. A window portion 23 and a through hole 2H are provided at the attachment portion 2X. A positioning protrusion 312 of the holder 3 is disposed on the inside of the window portion 23. An interlock pin 33 of the holder 3 is inserted through the through hole 2H. The treatment portion 2Y is provided on both the left and right sides of the attachment portion 2X, and the conductive layer 2a is exposed on the body-side portion 21 of the treatment portion 2Y.

The conductive layer 2a is also exposed on the surface facing the main body portion 4 at the attachment portion 2X, and the exposed portion constitutes a pad side electrode portion 22. The pad side electrode portion 22 is formed to establish an electrical connection with a main body portion side electrode portion 43, and the conductive layer 2a corresponding to one electrode portion (for example, a positive electrode) is exposed at one end of the attachment portion 2X, and the conductive layer 2a corresponding to the other electrode portion (for example, a negative electrode) is exposed at the other end of the attachment portion 2X.

Referring to FIG. 10, the holder 3 includes a pad holding portion 31 with a plate-like shape and a pair of wall portions 32 erected from both ends of the pad holding portion 31. The attachment portion 2X of the pad 2 is disposed on an upper surface 311 of the pad holding portion 31. Double-sided adhesive tape, glue, adhesive, or the like is disposed, as necessary, between the upper surface 311 and the attachment portion 2X.

The positioning protrusion 312 is provided on the pad holding portion 31. By fitting the inner peripheral edge of the window portion 23 provided in the pad 2 to the positioning protrusion 312, the pad 2 can be positioned with respect to the holder 3. The interlock pin 33 is centrally disposed on the pad holding portion 31. When attaching the pad 2 to the holder 3, the interlock pin 33 is inserted into the through hole 2H.

Referring to FIGS. 9 and 10, the main body portion 4 includes, as an outer cover, a case 4a with a substantially rectangular parallelepiped shape. A guiding/engagement portion 5 (FIG. 9) is formed between the case 4a and the holder 3, and the main body portion 4 (case 4a) is detachably attached to the holder 3. The guiding/engagement portion 5 is constituted by a protrusion 51 (FIG. 10) formed on a side surface 41 of the case 4a and a groove portion 52 (FIG. 10) formed in each of the wall portions 32 of the holder 3.

Referring to FIG. 10, the groove portion 52 includes a vertical groove portion 521 and a lateral groove portion 522. The vertical groove portion 521 is formed in the vertical direction and opens upward. The lateral groove portion 522 is formed in the lateral direction and opens at both ends. When the main body portion 4 is attached to the holder 3, both of the protrusion 51 and the groove portion 52 move closer together in a facing direction and engage together. By rotating and moving the main body portion 4 with respect to the holder 3, the engagement between the two is released, and the main body portion 4 can be removed from the holder 3.

With the main body portion 4 attached to the holder 3, the main body portion 4 supplies a low-frequency pulse current to the conductive layer 2a of the pad 2. Specifically, the main body portion 4 includes a pair of the main body portion side electrode portions 43, a substrate (not illustrated), an electric circuit (not illustrated), and an interlock mechanism (not illustrated). The electric circuit includes various control devices and is mounted on the surface of the substrate.

Examples of the control devices include a processor configured to perform various processes, a memory configured to store programs, data, and the like, a communication interface configured to wirelessly communicate various types of data with the terminal device 10, and a waveform generation/output device configured to boost the power source voltage and generating and outputting a low-frequency pulse current (treatment current).

The substrate, the electric circuit, and the interlock mechanism are provided inside the main body portion 4 (case 4a). A power source (not illustrated) such as a battery is also provided inside the main body portion 4 (case 4a). A switch 48S, a display portion (not illustrated) such as a light emitting diode (LED), and a button (not illustrated) are provided on the outside of the case 4a.

In a state in which the main body portion 4 is attached to the holder 3, an end portion of the main body portion side electrode portion 43 abuts the pad side electrode portion 22. Thus, the main body portion side electrode portion 43 and the pad side electrode portion 22 are electrically connected, whereby the electric circuit can supply a low-frequency pulse current to the pad side electrode portion 22.

Configuration of Terminal Device 10

Figure 11:
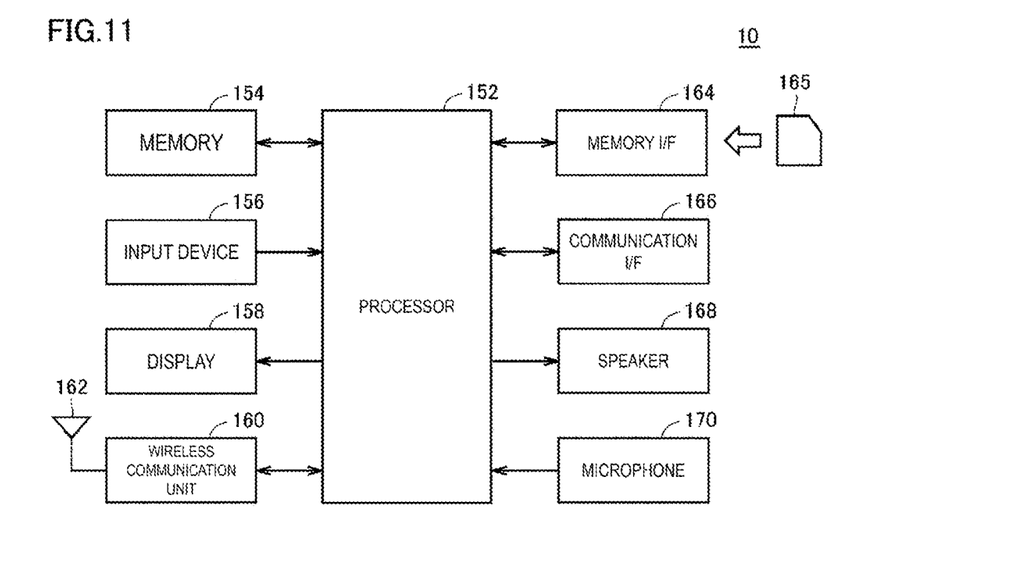
FIG. 11 is a block diagram illustrating an example of a hardware configuration of a terminal device according to the second embodiment.

FIG. 11 is a block diagram illustrating an example of a hardware configuration of the terminal device 10 according to the second embodiment. Referring to FIG. 11, the terminal device 10 includes, as main components, a processor 152, a memory 154, an input device 156, the display 158, a wireless communication unit 160, a memory interface (I/F) 164, a communication interface (I/F) 166, a speaker 168, and a microphone 170.

The processor 152 typically is an arithmetic processing unit such as a central processing unit (CPU) or a multi processing unit (MPU). The memory 154 is realized by random access memory (RAM), read-only memory (ROM), flash memory, and the like.

The input device 156 receives an operation input to the terminal device 10. Typically, the input device 156 is realized by a touch panel. The touch panel is provided on the display 158 that functions as a display portion, and is, for example, an electrostatic capacitive type. However, the input device 156 may include a button or the like.

The wireless communication unit 160 connects to a mobile communication network via a communication antenna 162 and transmits and receives signals for wireless communication. Accordingly, the terminal device 10 can communicate with other communication devices via a mobile communication network such as Long Term Evolution (LTE), for example.

The processor 152 reads the data stored in a storage medium 165 via the memory interface 164 and stores the data in the memory 154. The processor 152 reads the data from the memory 154 and stores the data in the external storage medium 165 via the memory interface 164.

The storage medium 165 may also be media that store programs in a non-volatile manner, such as a compact disc (CD), digital versatile disk (DVD), Blu-ray (trade name) disc (BD), universal serial bus (USB) memory, secure digital (SD) memory card.

The communication interface (I/F) 166 is a communication interface configured to exchange various data between the terminal device 10 and the electrical treatment device 20 and is realized by an adapter, a connector, or the like. As the communication method, for example, a wireless communication method such as Bluetooth low energy (BLE), and wireless LAN may be employed.

The speaker 168 converts an audio signal from the processor 152 to voice and outputs the same to the outside of the terminal device 10. The microphone 170 receives an audio input for the terminal device 10 and provides to the processor 152 an audio signal corresponding to the audio input.

Functional Configuration

The electrical treatment device 20 has a similar configuration to the treatment execution unit 304 and the difference calculation unit 306 among the configurations of the electrical treatment device 200 illustrated in FIG. 6. Each of these units are realized by a control device included in the main body portion 4 of the electrical treatment device 20. The operation unit 302 illustrated in FIG. 6 is realized by the processor 152 of the terminal device 10 and the input device 156.

In the first embodiment, the user provides instructions to the electrical treatment device 200 via the operation interface 230. In the second embodiment, the user provides various instructions to the terminal device 10 through the input device 156, and the instructions are sent from the terminal device 10 to the electrical treatment device 20. In this way, the various instructions are indirectly provided to the electrical treatment device 20. In other words, the electrical treatment device 20 receives an instruction input from the user through the terminal device 10. More specifically, the electrical treatment device 20 receives an instruction input from a user sent from the terminal device 10 via a communication interface. For example, the terminal device 10 receives operations for adjusting the electrical stimulation intensity and transmits a signal indicating the operation to the electrical treatment device 20. The electrical treatment device 20 adjusts the level of electrical stimulation intensity and changes the pulse frequency in response to an operation corresponding to the received signal.

Also, the first embodiment has a configuration in which the treatment current flows to the treatment site by a voltage being applied between the electrode of one of the pads 270 with a positive polarity and the electrode of the other pad 270 with a negative polarity. The second embodiment has a configuration in which two electrode portions are formed on one pad 2, the two electrode portions respectively corresponding to one having a positive polarity and the other having a negative polarity, and the treatment current flows to the treatment site by a pulse voltage waveform being applied between the electrodes.

Also, the various information is stored in the memory 220 used by the electrical treatment device 200 for various processes described above in the first embodiment, typically, such information is stored in the memory of the electrical treatment device 20. However, a portion of the information may be stored in the memory 154 of the terminal device 10. The electrical treatment device 20 has a configuration in which information necessary to notify the user, information to be stored in the terminal device 10, and the like are sent to the terminal device 10.

Other Embodiments (1) The first embodiment described above has a configuration using the pair of pads 270, but the configuration is not limited thereto. Some embodiments may have a configuration in which an electrode for positive polarity and an electrode for negative polarity are formed on a single pad.

(2) In the embodiment described above, a configuration has been described in which the pulse frequency is changed in response to an adjustment operation of the electrical stimulation intensity, but the pulse frequency may be changed only when the adjustment operation of the electrical stimulation intensity is an increase operation. In this case, for example, between steps S10 and S12 in FIG. 7, the electrical treatment device 200 provides a step of determining whether or not the adjustment operation is an increase operation. Then, if the adjustment operation is an increase operation, the electrical treatment device 200 performs the process from step S12 onward, and if the adjustment operation is a decrease operation, the electrical treatment device 200 changes the pulse voltage to correspond to the electrical stimulation intensity based on the decrease operation and terminates the process.

In other words, in the case in which the operation unit 302 receives an increase operation, the treatment execution unit 304 changes the pulse voltage to correspond to the electrical stimulation intensity based on the increase operation, changes the pulse frequency to the predetermined frequency Fs, and changes the frequency of the pulse voltage continuously or in a step-like manner from the predetermined frequency Fs. On the other hand, in the case in which the operation unit 302 receives a decrease operation, the treatment execution unit 304 changes the pulse voltage to correspond to the electrical stimulation intensity based on the decrease operation.

(3) In the embodiments described above, a program may be provided that causes a computer to function and execute controls such as those described in the flowcharts described above. Such a program can also be provided as a program product stored on a non-temporary computer-readable recording medium attached to a computer, such as a flexible disk, a compact disc read only memory (CD-ROM), a secondary storage device, a main storage device, and a memory card. Alternatively, a program may be provided, which is stored on a recording medium such as a hard disk built into a computer. The program may also be provided by download via a network.

(4) The configuration given as an example of the embodiment described above is an example configuration of the present invention. The configuration can be combined with other known technology, and parts thereof may be omitted or modified within the scope of the present invention. Furthermore, the processes and configurations of other embodiments may be employed as appropriate to the embodiments described above.

Supplementary Notes

As described above, the present embodiment includes disclosures such as described below.

Configuration 1

An electrical treatment device (200), comprising:
a plurality of electrodes that come into contact with a site of a body of a user;
an operation unit (302) that receives an operation for adjusting an electrical stimulation intensity provided to the site; and
a treatment execution unit (304) that applies a pulse voltage corresponding to the electrical stimulation intensity to the plurality of electrodes and performs treatment of the site by changing a frequency of the pulse voltage within a predetermined frequency range continuously or in a step-like manner, wherein
when the operation unit (302) receives the operation, the treatment execution unit (304) changes the pulse voltage to correspond to the electrical stimulation intensity based on the operation and changes the frequency of the pulse voltage to a predetermined frequency and changes the changed frequency of the pulse voltage from the predetermined frequency continuously or in a step-like manner.

Configuration 2

The electrical treatment device (200) according to configuration 1, wherein the predetermined frequency is a frequency other than a maximum frequency of the predetermined frequency range.

Configuration 3

The electrical treatment device (200) according to configuration 2, wherein the predetermined frequency is a minimum frequency of the predetermined frequency range.

Configuration 4

The electrical treatment device (200) according to configuration 2, wherein the predetermined frequency is a frequency at a predetermined time prior to a time point when a frequency of a pulse voltage reaches the maximum frequency.

Configuration 5

The electrical treatment device (200) according to any one of configuration 1 to 4, wherein the treatment execution unit (304) changes a frequency of a pulse voltage, in the frequency range, by sweeping the frequency in an increasing direction from a minimum frequency to a maximum frequency and then by sweeping the frequency in a decreasing direction from the maximum frequency to the minimum frequency.

Configuration 6

The electrical treatment device (200) according to any one of configurations 1 to 5, further comprising
a difference calculation unit (306) that, when the operation is received by the operation unit, calculates a difference frequency between a frequency of a pulse voltage just before the operation is received and the predetermined frequency, wherein
the treatment execution unit (304),
if the difference frequency is less than a threshold, changes the frequency of the pulse voltage to the predetermined frequency and changes the frequency of the pulse voltage from the predetermined frequency continuously or in a step-like manner and,
if the difference frequency is equal to or greater than the threshold, changes the frequency of the pulse voltage just before by only a predetermined value to approach the predetermined frequency and changes the frequency of the pulse voltage from a frequency after change continuously or in a step-like manner.

Configuration 7

The electrical treatment device (200) according to any one of configurations 1 to 6, wherein the electrical treatment device is a low-frequency treatment device.

Configuration 8

A treatment system (1), comprising:
an electrical treatment device (20) including a plurality of electrodes that come into contact with a site of a body of a user; and
a terminal device (10) capable of wireless communication with the electrical treatment device, wherein
the terminal device (10) receives an operation for adjusting an electrical stimulation intensity provided to the site and transmits a signal indicating the operation to the electrical treatment device (20);
the electrical treatment device (20) includes a treatment execution unit (304) that applies a pulse voltage corresponding to the electrical stimulation intensity to the plurality of electrodes and performs treatment of the site by changing a frequency of the pulse voltage within a predetermined frequency range continuously or in a step-like manner; and
when the operation is performed, the treatment execution unit (304) changes the pulse voltage to correspond to the electrical stimulation intensity based on the operation, changes the frequency of the pulse voltage to a predetermined frequency, and changes the frequency of the pulse voltage from the predetermined frequency continuously or in a step-like manner.

The embodiments described herein are illustrative in all respects and are not intended as limitations. The scope of the present invention is indicated not by the descriptions above but by the claims and includes all meaning equivalent to the scope and changes within the scope.

REFERENCE SIGNS LIST

1 Treatment system
2, 270 Pad
2H Through hole
2X Attachment portion
2Y Treatment portion
2a Conductive layer
3 Holder
4 Main body portion
4a Case
5 Guiding/engagement portion
10 Terminal device
20, 200 Electrical treatment device
21 Body-side portion
22 Pad side electrode portion
23 Window portion
30 Network
31 Pad holding portion
32 Wall portion
33 Interlock pin
40 Supporter
43 Main body portion side electrode portion
48S Switch
51 Protrusion
52 Groove portion
152, 210 Processor
154, 220 Memory
156 Input device
158, 260 Display
160 Wireless communication unit
162 Communication antenna
164 Memory interface
165 Storage medium
168 Speaker
170 Microphone
205 Control device
230 Operation interface
232 Power button
234 Mode selection button
236 Treatment start button
238 Adjustment button
240 Power source unit
250 Waveform generation/output device
280 Cord
282 Plug
302 Operation unit
304 Treatment execution unit
306 Difference calculation unit
312 Positioning protrusion
521 Vertical groove portion
522 Lateral groove portion

The invention claimed is:
1. An electrical treatment device, comprising:
a plurality of electrodes configured to come into contact with a site of a body of a user; and
a processor configured to:
receive an operation for adjusting an electrical stimulation intensity provided to the site;
apply a pulse voltage corresponding to the electrical stimulation intensity to the plurality of electrodes and perform treatment of the site by changing a frequency of the pulse voltage within a predetermined frequency range continuously or in a step-like manner, wherein
when the operation is received, the processor changes the pulse voltage to correspond to the electrical stimulation intensity based on the operation and changes the frequency of the pulse voltage to a predetermined frequency and changes the changed frequency of the pulse voltage from the predetermined frequency continuously or in a step-like manner,
when the operation is received, calculate a difference frequency between a frequency of a pulse voltage just before the operation is received and the predetermined frequency,
wherein if the difference frequency is less than a threshold, change the frequency of the pulse voltage to the predetermined frequency and change the frequency of the pulse voltage from the predetermined frequency continuously or in a step-like manner, and
wherein if the difference frequency is equal to or greater than the threshold, the processor is configured to change the frequency of the pulse voltage just before by only a predetermined value to approach but not meet the predetermined frequency and adjust the changed frequency continuously or in a step-like manner to approach but not meet the predetermined frequency.

2. The electrical treatment device according to claim 1, wherein
the predetermined frequency is a frequency other than a maximum frequency of the predetermined frequency range.

3. The electrical treatment device according to claim 2, wherein
the predetermined frequency is a minimum frequency of the predetermined frequency range.

4. The electrical treatment device according to claim 3, wherein
the processor is further configured to change a frequency of a pulse voltage, in the frequency range, by sweeping the frequency in an increasing direction from the minimum frequency to the maximum frequency and then by sweeping the frequency in a decreasing direction from the maximum frequency to the minimum frequency.

5. The electrical treatment device according to claim 3, wherein
the electrical treatment device is a low-frequency treatment device.

6. The electrical treatment device according to claim 2, wherein
the predetermined frequency is a frequency at a predetermined time prior to a time point when a frequency of a pulse voltage reaches the maximum frequency.

7. The electrical treatment device according to claim 6, wherein
the processor is further configured to change a frequency of a pulse voltage, in the frequency range, by sweeping the frequency in an increasing direction from a minimum frequency to the maximum frequency and then by sweeping the frequency in a decreasing direction from the maximum frequency to the minimum frequency.

8. The electrical treatment device according to claim 6, wherein
the electrical treatment device is a low-frequency treatment device.

9. The electrical treatment device according to claim 2, wherein
the processor is thither configured to change a frequency of a pulse voltage, in the frequency range, by sweeping the frequency in an increasing direction from a minimum frequency to the maximum frequency and then by sweeping the frequency in a decreasing direction from the maximum frequency to the minimum frequency.

10. The electrical treatment device according to claim 2, wherein
the electrical treatment device is a low-frequency treatment device.

11. The electrical treatment device according to claim 1, wherein
the processor is further configured to change a frequency of a pulse voltage, in the frequency range, by sweeping the frequency in an increasing direction from a minimum frequency to a maximum frequency and then by sweeping the frequency in a decreasing direction from the maximum frequency to the minimum frequency.

12. The electrical treatment device according to claim 11, wherein
the electrical treatment device is a low-frequency treatment device.

13. The electrical treatment device according to claim 1, wherein
the electrical treatment device is a low-frequency treatment device.

14. The electrical treatment device according to claim 1, wherein
the electrical treatment device is a low-frequency treatment device.

15. A treatment system, comprising:
an electrical treatment device including a plurality of electrodes that come into contact with a site of a body of a user; and
a terminal device including a terminal device processor capable of wireless communication with the electrical treatment device, wherein
the terminal device receives an operation for adjusting an electrical stimulation intensity provided to the site and transmits a signal indicating the operation to the electrical treatment device;
the electrical treatment device includes an electrical treatment device processor that applies a pulse voltage corresponding to the electrical stimulation intensity to the plurality of electrodes and performs treatment of the site by changing a frequency of the pulse voltage within a predetermined frequency range continuously or in a step-like manner; and
when the operation is performed, the processor changes the pulse voltage to correspond to the electrical stimulation intensity based on the operation and changes the frequency of the pulse voltage to a predetermined frequency and changes the changed frequency of the pulse voltage from the predetermined frequency continuously or in a step-like manner,
when the operation is received, calculate a difference frequency between a frequency of a pulse voltage just before the operation is received and the predetermined frequency,
wherein if the difference frequency is less than a threshold, change the frequency of the pulse voltage to the predetermined frequency and change the frequency of the pulse voltage from the predetermined frequency continuously or in a step-like manner, and
wherein if the difference frequency is equal to or greater than the threshold, the processor is configured to change the frequency of the pulse voltage just before by only a predetermined value to approach but not meet the predetermined frequency and adjust the changed frequency continuously or in a step-like manner to approach but not meet the predetermined frequency.

* * * * *